United States Patent [19]

Knifton

[11] Patent Number: 5,214,218
[45] Date of Patent: May 25, 1993

[54] ONE STEP SYNTHESIS OF METHYL T-BUTYL ETHER FROM T-BUTANOL USING HALOACID-MODIFIED CLAY CATALYSTS

[75] Inventor: John F. Knifton, Austin, Tex.

[73] Assignee: Texaco Chemical Company, White Plains, N.Y.

[21] Appl. No.: 878,121

[22] Filed: May 4, 1992

[51] Int. Cl.$^5$ ............................................. C07L 41/09
[52] U.S. Cl. ..................................................... 568/698
[58] Field of Search ......................................... 568/698

[56] References Cited

U.S. PATENT DOCUMENTS 4,605,806  8/1986  Ballantine et al. .................. 568/698
4,918,244  4/1990  Nelson et al. ....................... 568/698

*Primary Examiner*—Howard T. Mars
*Attorney, Agent, or Firm*—James L. Bailey; Kenneth R. Priem; Cynthia L. Kendrick

[57] ABSTRACT

A method is disclosed wherein t-butanol is reacted with methanol in a reaction zone in one step to provide methyl tert-butyl ether and the improvement of accomplishing the reaction which comprises:

a. Using a catalyst comprising a montmorillonite clay treated with a haloacid;
b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl tert-butyl ether product.

5 Claims, No Drawings

ONE STEP SYNTHESIS OF METHYL T-BUTYL ETHER FROM T-BUTANOL USING HALOACID-MODIFIED CLAY CATALYSTS

CROSS-REFERENCE

This application is related to U.S. Pat. Nos. 4,827,048; 4,822,921; 5,059,725 and 5,081,318 and to copending Application Ser. Nos. 07/494,280; 07/494,281; 07/724,071 and 07/745,777.

This invention concerns an improved process for preparing methyl tertiary-butyl ether (MTBE) by the reaction of tertiary-butanol and methanol in the presence of a catalyst comprising a haloacid-modified montmorillonite clay catalyst. MTBE has been generated in up to 40% concentration in the crude product. This catalyst demonstrates improved yields of MTBE product compared with unmodified montmorillonite clay. Another desirable feature is that the product mix separates into an isobutylene-MTBE product-rich phase and a heavier aqueous methanol phase at operating temperatures of 160° C. or greater.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, October 1984, p. 63; Oil and Gas J., Jan. 1, 1979, p. 76; Chem. Economics Handbook-SRI, September 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

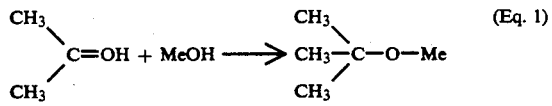

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary-butyl alcohol, since t-butanol (TBA) is readily available commercially through isobutane oxidation.

In U.S. Pat. No. 4,144,138 (1979) to Rao et al., there is disclosed a method for recovering methyl tertiary-butyl ether from etherification reaction effluent by azeotropic distillation to recover methanol-ether azeotrope overhead which is water-washed to give pure ether raffinate plus ether-methanol bottoms, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary-butyl ether over a catalyst comprising Kieselguhr impregnated with phosphoric acid at a temperature of about 175° F. to 350° F.

In an article titled "Catalysis: Selective Developments", Chem. Systems Report 84-3, 239-249, at section 3.4320, the unusual properties of smectite clays which make them of interest as catalysts are discussed. These compositions are layered and exhibit a 2:1 relationship between tetrahedral and octahedral sites. In addition the combination of cation exchange, intercalation and the fact that the distance between the layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

G. B. Patent No. 2,179,563 (1987) discloses the use of modified layered clay catalysts in reactions capable of catalysis by protons. Of particular interest in this invention were the three-layer sheet types, such as smectites, micas and vermiculites composed of successive layers of tetrahedral silica, octahedral alumina and tetrahedral silica which can exhibit swelling properties.

U.S. Pat. No. 4,590,294 (1986) discloses a process for the production of an ester comprising reacting an olefin from the group consisting of ethylene, hex-1-ene, hept-1-ene, oct-1-ene, 4-methylpent-1-ene, hex-2-ene, 1,5-hexadiene and cyclohexene with a carboxylic acid using as a catalyst component a hydrogen ion-exchanged layered clay. This reference would not seem to suggest a method for simultaneous dehydration of tert-butanol to isobutylene and the reaction with methanol to produce MTBE.

In U.S. Pat. No. 4,822,921 (1989), to which there was a cross-reference, there is disclosed a method for producing MTBE by reacting tertiary-butyl alcohol and methanol in the presence of a catalyst comprising an inert support, such as titania, having a phosphoric acid impregnated thereon.

U.S. Pat. No. 4,827,048 (1989), also referred to in the cross-references, discloses a method for producing MTBE by reacting tertiary-butyl alcohol and methanol in the presence of a catalyst comprising a heteropoly acid such as 12-tungstophosphoric acid or 12-molybdophosphoric acid on an inert support, such as titania.

In copending U.S. patent application Ser. No. 07/494,281, there is disclosed a method for preparing methyl tertiary-butyl ether by reacting butanol and methanol in the presence of a catalyst comprising a super-acid alumina or a faujasite-type zeolite.

Copending U.S. patent application Ser. No. 07/494,280 discloses the reaction of butanol and methanol in the presence of acidic montmorillonite clay catalysts having certain identifiable physical parameters, such as surface area, acidity range and moisture content.

In U.S. Pat. No. 5,081,318 (1992), there is described a one-step method for the synthesis of MTBE from t-butanol using a fluorosulfonic acid-modified zeolite catalyst.

In U.S. Pat. No. 5,059,725 (1991), a one-step synthesis for MTBE is disclosed wherein t-butanol and methanol is reacted over a catalyst comprising ammonium sulfate or sulfuric acid deposited upon a Group IV oxide.

In Ser. No. 07/724,071 a fluorocarbon sulfuric acid polymer on an inert support is disclosed for use as a catalyst for producing MTBE. And, in Ser. No. 07/745,777 there is disclosed the use of a hydrogen fluoride-modified zeolite catalyst for the production of MTBE.

With the current interest in the production of MTBE as blending component in high octane gasoline, the identification of novel catalysts which provide substantial yields are important in the art. If a catalyst provides substantial yields, also permits the production of MTBE in one step and incorporates the added feature of phase separation of the product above a certain temperature, such a catalyst represents a substantial advance in the art.

SUMMARY OF THE INVENTION

In accordance with certain of its aspects, the novel method of this invention for preparing methyl tert-butyl ether from tertiary-butyl alcohol (t-butanol) and methanol in one-step comprises reacting tertiary-butyl alcohol and methanol in the presence of a catalyst comprising a haloacid-modified montmorillonite clay at an elevated temperature and moderate pressure. Examples demonstrate particularly the effectiveness of montmorillonite clays modified with haloaliphatic carboxylic acids, haloaromatic carboxylic acids, haloaliphaticsulfonic acids, haloaromaticsulfonic acids and hydrogen chloride.

DESCRIPTION OF THE INVENTION

Preparation of the product of this invention may be carried out typically by reacting tertiary-butyl alcohol and methanol in the presence of an etherification catalyst. The etherification is carried out in one step and the catalyst preferably comprises a haloacid-modified montmorillonite clay.

The reaction can be represented by the following:

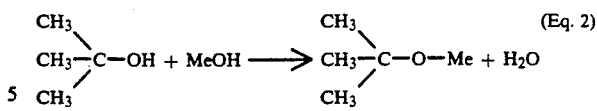

Generally the methanol and t-butanol coreactants may be mixed in any proportion in order to generate the desired methyl t-butyl ether, but preferably the molar ratio of methanol to t-butanol in the feed mixture should be between 10:1 and 1:10, the yield of desired MTBE is to be maximized. In order to achieve maximum selectivity to MTBE, and optimum conversion per pass, an excess of methanol in the liquid feed is desirable. The most preferred methanol-to-tertiary-butanol molar ratio is from 1:1 to 5:1. Optionally, said t-butanol plus methanol feed mixtures may be crude feedstocks containing other components, including water, ketones such as acetone, other alcohols such as 2-propanol, peroxides such as di-t-butyl peroxide, t-butyl hydroperoxide and allyl t-butyl peroxide, esters such as t-butyl formate, as well as methyl t-butyl ether product.

In certain circumstances, it may be particularly desirable that the TBA conversion be high enough (e.g. >40% per pass), such that the crude product mix phase separates into an isobutylene-MTBE product-rich phase and a heavier aqueous methanol phase. Preferably such a product phase separation would be achieved at as low an etherification temperature as possible, but particularly in the range 160°–200° C.

The same process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary-butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

Good results were realized using certain haloacid-modified clays as catalysts for the reaction in Eq. 2, particularly haloaliphatic carboxylic acid and haloaromatic carboxylic acid clays.

The clays used to form this catalyst are silica-alumina clays. Chemically, clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in reaction (Eq. 2) are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, where the distance between the layers can be adjusted by swelling. This layering is illustrated in an article by F. Figueras, Catal. Rev.-Sci. Eng., 30, 457 (1988). What renders the smectites of interest among the clay minerals is the combination of cation exchange, intercalation, and the fact that the distance between the layers can be adjusted by treatment with the appropriate solvent etc.

The three layered sheet types include montmorillonite, vermiculite and some brittle mica. The idealized basic structure of clays of this type is that of a pyrophyllite which has the basic formula $Si_8Al_4O_{20}(OH)_4$.

A general representation of the montmorillonite structure is:

Where: M represents the interlamellar (balancing cations), normally sodium or lithium and x, y and n are integers.

Said montmorillonite clays are best treated with haloacid as demonstrated in Examples 1 and 2.

Haloacids useful for modifying the montmorillonite clays are selected from the group consisting of halophosphoric acids, haloaliphatic carboxylic acids, haloaromatic carboxylic acids, haloaromaticsulfonic acids, haloaliphaticsulfonic acids and hydrogen chloride. Examples include halophosphoric and halophosphorous acids such as difluorophosporic acid and fluorophosphoric acids, haloaliphatic carboxylic acids such as trifluoroacetic acid, pentafluoropropionic acid and trichloroacetic acid, haloaromatic carboxylic acids such as pentafluorobenzoic acid and pentafluorophenylacetic acid; haloaromaticsulfonic acids such as the fluorobenzenesulfonic acids as well as the sulfonyl chloride derivatives thereof, such as pentafluorobenzenesulfonyl chloride, as well as hydrogen chloride, hydrochloric acid, and haloaliphaticsulfonic acids such as trichloromethanesulfonic acid or derivatives thereof such as trichloromethanesulfonyl chloride.

The montmorillonite clays to be modified may be in the form of powders, pellets, granules, spheres, shapes and extrudates. The examples described herein demonstrate certain advantages using powders. An example of a commercially-available, neutral, montmorillonite clay which can be treated with a haloacid is Engelhard Grade 2C Powder.

Preparation of the haloacid-modified clay is accomplished by adding a solution of the haloacid in distilled water, or in an organic solvent, such as acetone, to the neutral clay which is preferably in powdered form. The mixture is then stirred for from about one to 48 hours, under a nitrogen blanket, washed with distilled water and/or an appropriate organic solvent, and dried in vacuo at from about 20° to 100° C., followed by 20° to 300° C. Said haloacid-modified clays generally have titratable acidities up to 1 meq/g or higher.

It has been discovered that haloacid-modified clays possess a number of improved properties for the production of MTBE. The performance of representative haloacid-modified clays in MTBE synthesis from t-butanol and methanol in one-step (Eq. 2) is illustrated by the accompanying examples.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. The total operating pressure may be from 0 to 1000 psig, or higher. The preferred pressure range is 50 to 500 psig.

Typically, MTBE is generated continuously in up to about 40 wt % concentration in the crude liquid product at total liquid hourly space velocities (LHSV) of up to 5 or higher and relatively mild conditions, where:

$$LHSV = \frac{\text{Volume of Total Liquid Feed Run Through The Reactor Per Hour}}{\text{Volume of Catalyst In Reactor}}$$

Conversions of t-butanol (TBA, wt %) are estimated in the following examples using the equation:

$$\frac{(\text{Wt \% Conc. of } TBA \text{ in Feed} - \text{Wt \% Conc. of } TBA \text{ in Product})}{\text{Wt \% Conc. of } TBA \text{ in Feed}} \times 100$$

Selectivities of methyl t-butyl ether (MTBE, mole %) and isobutylene ($C_4H_8$, mole %) are estimated from:

$$\frac{\text{Moles of } MTBE \text{ (or } C_4H_8\text{) in Product}}{\text{moles of } TBA \text{ converted}} \times 100$$

The examples which follow illustrate the one-step synthesis of MTBE from TBA and MeOH (Eq. 2) using haloacid-modified clays particularly in powdered form. The examples are only intended as a means of illustration and it is understood the invention is not meant to be limited thereby.

The following can be noted:

1) Examples 1 and 2 illustrate the synthesis of trichloroacetic acid and trifluoroacetic acid-modified clays.

2) In Example 3, the trichloroacetic acid-modified clay of Example 1 gave MTBE in 40 wt % concentration when utilized in a continuous reactor system at LHSV of 2 (e.g. Sample 1, Table 1) using a low MeOH/tBA molar feed ratio of 1.1:1. Under these conditions the tBA conversion is 66% at 120° C., but 90% at 160° C. Experiments at both 160° and 180° C. give crude liquid products that are surprisingly separated into an isobutylene-MTBE rich phase and a heavier aqueous methanol phase.

3) In Examples 4–10, a series of haloacid-modified montmorillonite clay samples were demonstrated to be effective solid acid catalysts for MTBE/isobutylene cosynthesis.

These suitable haloacids include:

a) Haloaliphatic carboxylic acids such as pentafluoropropionic acid and trifluoroacetic acid (Examples 4 and 5).

b) Haloaromatic carboxylic acids such as pentafluorophenylacetic acid and pentafluorobenzoic acid (Examples 7 and 9).

c) Haloaromaticsulfonic acids such as fluorobenzenesulfonic acids and their sulfonyl chloride derivatives, e.g., pentafluorobenzene sulfonyl chloride (Example 6).

d) Haloaliphaticsulfonic acids and their derivatives, e.g., trichloromethanesulfonic acid and its sulfonyl chloride derivatives, such as trichloromethanesulfonyl chloride (Example 10).

e) Hydrogen chloride (Example 8).

4. In comparison Example A, the unmodified montmorillonite clay gave low MTBE concentration in the product effluent and only 25% to tBA conversion per pass at 160° C. (Sample 6, Table 9).

EXAMPLE 1

This example illustrates the preparation of a trichloroacetic acid-modified montmorillonite clay.

To 100 g of a neutral montmorillonite clay (Englehard Grade 2C Powder) was added an aqueous solution of trichloroacetic acid (10.0 g) in distilled water (100 cc). The mixture was stirred for 24 hours under a nitrogen blanket, filtered and the solids washed with distilled water then dried in vacuo at 40° C. for 4 hours followed by 150° C. overnight.

The recovered white powder was found to comprise by analysis:
$H_2O = 1.1\%$
Acidity = 0.11 meq/g

EXAMPLE 2

This example illustrates the preparation of a trifluoroacetic acid-modified montmorillonite clay.

To 100 g of a neutral montmorillonite clay (Englehard Grade 2C Powder, dried at 175° C. in vacuo) was added a solution of trifluoroacetic acid (10.0 g) in dried acetone (100 cc). The mixture was stirred for 24 hours under a nitrogen blanket, filtered and the solids first washed with acetone and water, then dried in vacuo at 40° C. overnight, followed by 150° C. for 4 hours.

The recovered white powder was found to comprise by analysis:
$H_2O = 0.7\%$
Acidity = 0.12 meq/g

EXAMPLE 3

This example illustrates the production of methyl t-butyl ether from t-butanol and methanol using a trichloroacetic acid-modified montmorillonite clay.

Synthesis was conducted in a tubular reactor (½" i.d., 12" long), constructed at 316 ss, operated upflow and mounted in a furnace controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of trichloroacetic acid modified clay powder, prepared by the method of Example 1. A screen of glass wool was placed at the top and bottom of the reactor to ensure the catalyst would remain in the middle portion.

The catalyst bed was treated with a methanol/t-butanol (1.1:1 molar mix) upflow, at a flow rate of 50 cc/hr, while the reactor was held at 120° C., with a total pressure of 300 psi. Samples of crude product effluent were collected periodically on-stream, in 316 ss bombs and analyzed by glc and gc-ir.

Typically analyses data for samples taken under these conditions are summarized in Table 1. Performance at a series of other temperatures (140°, 160° and 180° C.) was determined using the same procedure. These results are also given in Table 1.

Of note, conversion levels and isobutylene/MTBE selectivities at 120° C. and 160° C. are as follows:

| Sample | Operating Temp (°C.) | tBA Conv (%) | Molar Selectivity (%) $C_4H_8$ | MTBE |
|---|---|---|---|---|
| 1 | 120 | 66 | 23 | 75 |
| 5 | 160 | 90 | a | a |

<sup>a</sup>Not determined.

TABLE 1

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) $H_2O$ | MeOH | $C_4H_8$ | tBA | MTBE |
|---|---|---|---|---|---|---|---|---|---|---|---|
| 3 | Ex. 1 | 1.1:1 | 50 | | | FS-1 | | | | | |
| | | | | 120 | 1 | 1 | 11.4 | 17.2 | 7.8 | 23.2 | 40.1 |
| | | | | | | 2 | 11.5 | 17.1 | 7.7 | 23.3 | 40.1 |
| | | | | 140 | 2 | 3 | 12.5 | 19.1 | 11.8 | 20.8 | 35.5 |
| | | | | | | 4 | 12.6 | 19.1 | 11.9 | 20.6 | 35.5 |
| | | | | 160 | 3 | 5 | 2.8 | 11.6 | 52.0 | 6.2 | 27.2 |
| | | | | | | | 33.6 | 46.6 | 4.5 | 7.7 | 7.2 |
| | | | | | | 6 | 2.8 | 11.4 | 52.5 | 5.8 | 27.2 |
| | | | | | | | 32.7 | 47.5 | 4.5 | 7.4 | 7.4 |
| | | | | 180 | 4 | 7 | 1.6 | 7.7 | 71.7 | 2.9 | 16.0 |
| | | | | | | | 33.6 | 52.4 | 4.5 | 5.7 | 4.2 |
| | | | | | | 8 | 1.3 | 7.4 | 72.3 | 2.9 | 16.0 |
| | | | | | | | 32.2 | 52.2 | 4.7 | 6.0 | 4.3 |

EXAMPLES 4-10

In these examples, following the procedures of Example 3, a series of haloacid-modified montmorillonite clays were evaluated for the cosynthesis of MTBE plus isobutylene from t-butanol/methanol (1:1.1 mixtures).

The results are summarized in the accompanying Tables 2-8.

TABLE 2

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) $H_2O$ | MeOH | $C_4H_8$ | tBA | MTBE |
|---|---|---|---|---|---|---|---|---|---|---|---|
| 4 | Pentafluoropropionic Acid on Clay 2C | 1.1:1 | 50 | | | FS-1 | | 31.0 | | 68.0 | |
| | | | | 120 | 1 | 1 | 9.4 | 19.9 | 7.1 | 30.8 | 32.5 |
| | | | | | | 2 | 8.9 | 20.8 | 6.6 | 33.5 | 29.9 |
| | | | | 140 | 2 | 3 | 10.9 | 19.4 | 9.9 | 25.8 | 33.6 |
| | | | | | | 4 | 10.6 | 19.7 | 9.7 | 26.8 | 32.8 |

TABLE 2-continued

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | H$_2$O | MeOH | C$_4$H$_8$ | tBA | MTBE |
| | | | | 160 | 3 | 5 | 12.9 | 20.1 | 17.6 | 17.4 | 31.6 |
| | | | | | | 6 | 13.3 | 20.4 | 16.8 | 18.1 | 31.1 |
| | | | | 180 | 4 | 7 { | 6.2 | 16.9 | 34.8 | 11.0 | 30.8 |
| | | | | | | | 35.7 | 40.5 | 4.3 | 9.7 | 9.4 |
| | | | | | | 8 { | 5.9 | 16.1 | 36.4 | 10.4 | 30.9 |
| | | | | | | | 35.5 | 40.7 | 4.5 | 9.5 | 9.4 |

TABLE 3

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | H$_2$O | MeOH | C$_4$H$_8$ | tBA | MTBE |
| 5 | Ex. 2 | 1.1:1 | 50 | | | FS-1 | | 31.6 | | 68.0 | |
| | | | | 120 | 1 | 1 | 7.6 | 23.5 | 5.4 | 41.3 | 22.0 |
| | | | | | | 2 | 7.0 | 24.0 | 5.3 | 42.6 | 20.9 |
| | | | | 140 | 2 | 3 | 11.1 | 19.8 | 10.1 | 24.3 | 34.4 |
| | | | | | | 4 | 11.3 | 19.7 | 10.4 | 23.4 | 35.0 |
| | | | | 160 | 3 | 5 | 12.9 | 21.0 | 17.7 | 16.1 | 32.1 |
| | | | | | | 6 | 13.1 | 20.5 | 18.1 | 15.9 | 32.2 |
| | | | | 180 | 4 | 7 { | 7.0 | 18.6 | 34.6 | 12.1 | 27.4 |
| | | | | | | | 32.3 | 40.0 | 5.7 | 11.4 | 10.3 |
| | | | | | | 8 { | 8.5 | 20.1 | 31.1 | 13.2 | 26.8 |
| | | | | | | | 31.8 | 39.2 | 6.0 | 12.0 | 10.7 |

TABLE 4

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | H$_2$O | MeOH | C$_4$H$_8$ | tBA | MTBE |
| 6 | Pentafluoro-benzene-sulfonyl Chloride on Clay 2C | 1.1:1 | 50 | | | FS-1 | | 31.4 | | 68.6 | |
| | | | | 120 | 1 | 1 | 2.9 | 28.7 | 2.6 | 58.2 | 7.4 |
| | | | | | | 2 | 2.5 | 29.1 | 2.3 | 59.5 | 6.3 |
| | | | | 140 | 2 | 3 | 5.6 | 25.9 | 4.8 | 48.2 | 15.2 |
| | | | | | | 4 | 5.3 | 26.0 | 4.8 | 48.6 | 15.1 |
| | | | | 160 | 3 | 5 | 10.3 | 21.9 | 10.4 | 27.6 | 29.6 |
| | | | | | | 6 | 10.1 | 21.8 | 10.6 | 29.5 | 27.7 |
| | | | | 180 | 4 | 7 { | 8.9 | 19.9 | 27.9 | 13.4 | 29.7 |
| | | | | | | | 34.8 | 38.3 | 4.7 | 11.1 | 10.9 |
| | | | | | | 8 { | 8.6 | 14.7 | 26.4 | 15.9 | 34.1 |
| | | | | | | | 34.5 | 38.3 | 4.8 | 11.1 | 11.0 |

TABLE 5

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | H$_2$O | MeOH | C$_4$H$_8$ | tBA | MTBE |
| 7 | Pentafluoro-phenylacetic Acid on Clay 2C | 1.1:1 | 50 | | | FS-1 | | 31.5 | | 68.3 | |
| | | | | 120 | 1 | 1 | 1.0 | 30.5 | 1.0 | 63.3 | 1.9 |
| | | | | | | 2 | 0.8 | 30.6 | 0.9 | 65.8 | 1.7 |
| | | | | 140 | 2 | 3 | 4.1 | 27.0 | 3.9 | 53.2 | 11.4 |
| | | | | | | 4 | 4.1 | 27.2 | 3.9 | 53.6 | 10.9 |
| | | | | 160 | 3 | 5 | 9.1 | 22.1 | 9.2 | 34.7 | 24.7 |
| | | | | | | 6 | 9.1 | 22.4 | 9.2 | 34.6 | 24.5 |
| | | | | 180 | 4 | 7 | 12.6 | 21.6 | 21.2 | 15.7 | 28.5 |
| | | | | | | 8 | 12.7 | 21.5 | 21.4 | 51.1 | 29.0 |

TABLE 6

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | $H_2O$ | MeOH | $C_4H_8$ | tBA | MTBE |
| 8 | HCl on Clay 2C | 1.1:1 | 50 | | | FS-1 | | 31.5 | | 68.1 | |
| | | | | 120 | 1 | 1 | 11.5 | 17.9 | 7.0 | 23.0 | 40.3 |
| | | | | | | 2 | 11.5 | 17.6 | 7.1 | 22.8 | 40.7 |
| | | | | 140 | 2 | 3 | 12.6 | 20.0 | 11.7 | 19.1 | 36.2 |
| | | | | | | 4 | 12.2 | 20.7 | 11.3 | 21.0 | 33.5 |
| | | | | 160 | 3 | 5 { | 2.0 | 10.5 | 55.8 | 5.0 | 26.4 |
| | | | | | | | 34.8 | 47.5 | 3.6 | 7.1 | 6.7 |
| | | | | | | 6 { | 2.1 | 10.8 | 54.8 | 5.7 | 26.3 |
| | | | | | | | 33.6 | 47.6 | 3.9 | 7.6 | 6.9 |
| | | | | 180 | 4 | 7 { | 0.8 | 9.2 | 72.9 | 2.7 | 14.0 |
| | | | | | | | 36.8 | 52.3 | 2.7 | 5.1 | 2.7 |
| | | | | | | 8 { | 1.1 | 9.4 | 72.2 | 2.5 | 14.4 |
| | | | | | | | 36.4 | 52.8 | 2.7 | 5.2 | 2.7 |

TABLE 7

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | $H_2O$ | MeOH | $C_4H_8$ | tBA | MTBE |
| 9 | Pentafluoro-benzoic Acid on Clay 2C | 1.1:1 | 50 | | | FS-1 | | 31.0 | | 68.8 | |
| | | | | 120 | 1 | 1 | 3.1 | 26.9 | 3.0 | 55.9 | 10.9 |
| | | | | | | 2 | 2.9 | 26.9 | 2.9 | 56.5 | 10.5 |
| | | | | 140 | 2 | 3 | 7.3 | 22.6 | 6.7 | 39.2 | 24.0 |
| | | | | | | 4 | 7.0 | 23.2 | 6.6 | 39.4 | 23.5 |
| | | | | 160 | 3 | 5 | 10.7 | 20.5 | 12.1 | 25.7 | 30.8 |
| | | | | | | 6 | 10.5 | 20.7 | 11.5 | 26.4 | 30.5 |
| | | | | 180 | 4 | 7 { | 10.9 | 20.7 | 24.8 | 14.5 | 28.8 |
| | | | | | | | 36.1 | 35.4 | 4.9 | 11.9 | 11.5 |
| | | | | | | 8 { | 10.9 | 20.6 | 24.8 | 14.6 | 28.8 |
| | | | | | | | 36.0 | 35.3 | 4.8 | 11.9 | 11.6 |

TABLE 8

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | Product Composition (wt %) | | | | |
|---|---|---|---|---|---|---|---|---|---|---|---|
| | | | | | | | $H_2O$ | MeOH | $C_4H_8$ | tBA | MTBE |
| 10 | Trichloro-methane-sulfonyl Chloride on Clay 2C | 1.1:1 | 50 | | | FS-1 | | | | | |
| | | | | 120 | 1 | 1 | 1.5 | 29.5 | 1.8 | 61.4 | 5.7 |
| | | | | | | 2 | 1.5 | 29.5 | 1.7 | 61.8 | 5.3 |
| | | | | 140 | 2 | 3 | 5.6 | 25.0 | 5.6 | 44.8 | 18.8 |
| | | | | | | 4 | 5.5 | 25.3 | 5.4 | 45.3 | 18.4 |
| | | | | 160 | 3 | 5 | 10.5 | 20.7 | 11.4 | 26.7 | 30.5 |
| | | | | | | 6 | 10.2 | 20.6 | 11.5 | 26.4 | 30.7 |
| | | | | 180 | 4 | 7 { | 6.0 | 16.5 | 34.2 | 10.5 | 32.6 |
| | | | | | | | 38.0 | 39.0 | 3.8 | 9.0 | 10.0 |
| | | | | | | 8 { | 6.0 | 16.4 | 34.6 | 10.3 | 32.5 |
| | | | | | | | 37.7 | 39.0 | 4.0 | 9.2 | 9.9 |

COMPARATIVE EXAMPLE A

This comparative example illustrates the performance of unmodified montmorillonite clay in the production of methyl t-butyl ether from t-butanol and methanol.

Using the equipment and procedures of Example 3, 25 cc of untreated montmorillonite clay (Englehard Grade 2C Clay Powder) was charged to the reactor system and performance was monitored over a series of temperatures (120°, 140°, 160° and 180° C.). The tBA/-MeOH (1:1.1) feed rate was maintained at 50 cc/hr. The results are summarized in Table 9.

Calculated tBA conversion and $C_4H_8$/MTBE selectivities for Samples 2 and 6 are as follows:

| Sample | Operating Temp (°C.) | tBA Conv (%) | Molar Selectivity (%) | |
|---|---|---|---|---|
| | | | $C_4H_8$ | MTBE |
| 2 | 120 | <1 | | |
| 6 | 160 | 25 | 34 | 63 |

TABLE 9

| Ex. | Catalyst | MeOH/tBA Molar Ratio | Temp. (°C.) | Feed Rate (cc/hr) | Time On Stream (Days) | Sample | Product Composition (wt %) | | | | |
|---|---|---|---|---|---|---|---|---|---|---|---|
| | | | | | | | $H_2O$ | MeOH | $C_4H_8$ | tBA | MTBE |
| A | Clay-2C | | | | | FS-1 | | 31.4 | | 67.9 | |
| | | 1.1 | 120 | 50 | 1 | 1 | 0.1 | 31.4 | 0.2 | 67.7 | 0.4 |
| | | | | | | 2 | 0.2 | 31.3 | 0.3 | 67.4 | 0.6 |
| | | | 140 | 50 | 2 | 3 | 1.3 | 30.7 | 1.0 | 63.9 | 2.9 |
| | | | | | | 4 | 0.8 | 30.8 | 0.9 | 64.7 | 2.5 |
| | | | 160 | 50 | 3 | 5 | 3.0 | 28.2 | 3.5 | 55.5 | 9.5 |
| | | | | | | 6 | 4.4 | 27.3 | 4.5 | 50.6 | 12.9 |
| | | | 180 | 50 | 4 | 7 | 10.0 | 22.1 | 12.8 | 26.5 | 28.2 |
| | | | | | | 8 | 9.9 | 22.4 | 12.6 | 26.9 | 27.9 |

What is claimed is:

1. In a method wherein t-butanol is reacted with methanol in a one step in the presence of a catalyst to provide methyl tert-butyl ether, the improvement comprising using as a catalyst a montmorillonite clay modified with a haloacid from the group consisting of haloaliphatic carboxylic acids selected from the group consisting of trifluoroacetic acid, pentafluoropropionic acid and trichloroacetic acid, haloaromatic carboxylic acids selected from the group consisting of pentafluorobenzoic acid and pentafluorobenzeneacetic acid, haloaromaticsulfonic acids selected from the group consisting of fluorobenzenesulfonic acids and sulfonyl chloride derivatives thereof, and haloaliphaticsulfonic acids selected from the group consisting of trichlormethanesulfonic acid and a sulfonyl chloride derivative thereof, and continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain methyl tert-butyl ether product.

2. The method of claim 1 wherein the temperature is from about 80° C. to about 200° C.

3. The method of claim 1 wherein the operating temperature is in the range 160° to 200° C. and the product comprises a two-phase mix of an isobutylene-MTBE product-rich phase and a heavier aqueous methanol-rich phase.

4. The method of claim 1 wherein said montmorillonite clay has the structure:

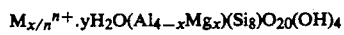

$$M_{x/n}^{n+} \cdot yH_2O(Al_{4-x}Mg_x)(Si_8)O_{20}(OH)_4$$

Where: M represents the interlamellar balancing cations, normally sodium or lithium and x, y and n are integers.

5. The method of claim 1 wherein the haloacid-treated clay has an acidity in the range 0–1 meq/g.

* * * * *